United States Patent
Nelson et al.

(10) Patent No.: US 11,980,664 B2
(45) Date of Patent: *May 14, 2024

(54) TOOTHPASTE FOR DELIVERING ALLERGENS TO ORAL MUCOSA

(71) Applicant: Allovate, LLC, New York, NY (US)

(72) Inventors: Michael Nelson, New York, NY (US); Erick Berglund, New York, NY (US)

(73) Assignee: ALLOVATE, LLC, New York, NY (US)

( * ) Notice: Subject to any disclaimer, the term of this patent is extended or adjusted under 35 U.S.C. 154(b) by 140 days.

This patent is subject to a terminal disclaimer.

(21) Appl. No.: 17/194,660

(22) Filed: Mar. 8, 2021

(65) Prior Publication Data

US 2021/0187103 A1 Jun. 24, 2021

Related U.S. Application Data

(60) Continuation of application No. 16/659,875, filed on Oct. 22, 2019, now Pat. No. 10,967,059, which is a division of application No. 15/022,249, filed as application No. PCT/US2014/056562 on Sep. 19, 2014, now Pat. No. 10,485,867.

(60) Provisional application No. 61/879,801, filed on Sep. 19, 2013, provisional application No. 61/879,779, filed on Sep. 19, 2013.

(51) Int. Cl.
| | |
|---|---|
| *A61K 39/35* | (2006.01) |
| *A61K 8/34* | (2006.01) |
| *A61K 8/64* | (2006.01) |
| *A61K 8/9728* | (2017.01) |
| *A61K 8/9789* | (2017.01) |
| *A61K 8/9794* | (2017.01) |
| *A61K 8/98* | (2006.01) |
| *A61K 39/00* | (2006.01) |
| *A61K 49/00* | (2006.01) |
| *A61Q 11/00* | (2006.01) |

(52) U.S. Cl.
CPC ............. *A61K 39/35* (2013.01); *A61K 8/345* (2013.01); *A61K 8/64* (2013.01); *A61K 8/9728* (2017.08); *A61K 8/9789* (2017.08); *A61K 8/9794* (2017.08); *A61K 8/981* (2013.01); *A61K 8/985* (2013.01); *A61K 8/987* (2013.01); *A61K 49/0004* (2013.01); *A61Q 11/00* (2013.01); *A61K 2039/542* (2013.01); *A61K 2039/55* (2013.01); *A61K 2039/552* (2013.01); *A61K 2800/882* (2013.01); *A61K 2800/92* (2013.01)

(58) Field of Classification Search
CPC .......... A61K 39/35; A61K 8/345; A61K 8/64; A61K 8/981; A61K 49/0004; A61K 2039/552; A61K 2800/882; A61K 2800/92; A61K 8/97; A61K 8/99; A61K 9/006; A61Q 11/00; A61P 11/02; A61P 37/04; A61P 27/14; A61P 37/08

See application file for complete search history.

(56) References Cited

U.S. PATENT DOCUMENTS

| | | |
|---|---|---|
| 6,042,812 A | 3/2000 | Sanker et al. |
| 6,113,887 A | 9/2000 | Mori et al. |
| 6,780,416 B1 | 8/2004 | Spertini |
| 6,821,507 B2 | 11/2004 | Giandorf et al. |
| 7,300,645 B2 | 11/2007 | Takatsuka et al. |
| 7,367,476 B2 | 5/2008 | Law et al. |
| 7,654,418 B2 | 2/2010 | Law et al. |
| 7,690,535 B2 | 4/2010 | Law et al. |
| 7,887,821 B2 | 2/2011 | Jacobi et al. |
| 7,891,522 B2 | 2/2011 | Law et al. |
| 8,329,196 B2 | 12/2012 | Jacobi et al. |
| 8,459,046 B2 | 6/2013 | Richter-Friis et al. |
| 8,631,975 B2 | 1/2014 | Lim |
| 9,408,805 B2 | 8/2016 | Jacobi et al. |
| 10,080,719 B2 | 9/2018 | Jacobi et al. |
| 2003/0118648 A1 | 6/2003 | Hirsh et al. |
| 2004/0166123 A1 | 8/2004 | Jacobi et al. |
| 2004/0191276 A1 | 9/2004 | Muni |
| 2004/0241107 A1 | 12/2004 | Burzynski et al. |
| 2005/0084551 A1* | 4/2005 | Jensen ................. A61K 8/9794 424/769 |

(Continued)

FOREIGN PATENT DOCUMENTS

| | | |
|---|---|---|
| JP | H0959179 A | 3/1997 |
| KR | 20080070851 A | 7/2008 |

(Continued)

OTHER PUBLICATIONS

AU Examination Report No. 1 dated Oct. 18, 2022 pertaining to AU divisional application No. 2021217993 filed Aug. 16, 2021, pp. 1-2.

(Continued)

*Primary Examiner* — Snigdha Maewall
(74) *Attorney, Agent, or Firm* — Dinsmore & Shohl LLP

(57) ABSTRACT

Pro-toothpaste compositions formulated to receive a volume of allergen solution to provide toothpastes that exhibit efficacy for oral mucosal immunotherapy (OMIT) and acceptable consumer and product stability properties, along with kits of pro-toothpaste, allergen/extracts of allergens, and optionally compounding means and/or specialized toothbrushes are provided. Toothpastes suitable and effective for OMIT and methods for managing allergic symptoms and for reducing risk of allergy in people without symptoms employing the pro-toothpastes, toothpastes and kits of the invention are also disclosed.

20 Claims, 2 Drawing Sheets

(56) References Cited

U.S. PATENT DOCUMENTS

| | | |
|---|---|---|
| 2005/0197319 A1 | 9/2005 | Nonomura et al. |
| 2006/0140879 A1 | 6/2006 | Fruge et al. |
| 2006/0171968 A1 | 8/2006 | Brimnes et al. |
| 2006/0287263 A1 | 12/2006 | Davis et al. |
| 2007/0031539 A1 | 2/2007 | Carlton, Jr. |
| 2007/0110673 A1 | 5/2007 | Spertini et al. |
| 2007/0219153 A1 | 9/2007 | Kandimalla et al. |
| 2008/0152695 A1 | 6/2008 | Clark et al. |
| 2008/0302682 A1 | 12/2008 | Engstrom et al. |
| 2009/0117083 A1 | 5/2009 | Nash et al. |
| 2009/0214597 A1 | 8/2009 | Moldt et al. |
| 2010/0018540 A1 | 1/2010 | Doolittle et al. |
| 2010/0183523 A1 | 7/2010 | Wagner |
| 2011/0142867 A1 | 6/2011 | Larche et al. |
| 2012/0128734 A1 | 5/2012 | Hubinette et al. |
| 2013/0149670 A1* | 6/2013 | Francois ............... A61K 39/36 424/48 |
| 2017/0087231 A1 | 3/2017 | Arshad et al. |
| 2017/0367970 A1 | 12/2017 | Jacobi et al. |

FOREIGN PATENT DOCUMENTS

| | | |
|---|---|---|
| WO | 1993001213 | 1/1993 |
| WO | 2007-51476 A1 | 5/2007 |
| WO | 2007084587 A2 | 7/2007 |
| WO | 2008098749 | 8/2008 |
| WO | 2008156704 | 12/2008 |
| WO | 2010128364 | 11/2010 |
| WO | 2011137420 A1 | 11/2011 |
| WO | 2015042402 A1 | 3/2015 |

OTHER PUBLICATIONS

Asturias, J.A. et al, Tolerance and immunological changes of chemically modified allergen vaccine of Parietaria judaica in accelerated schedules; Clinical and Experimental Immunology, Dec. 5, 2006, 147: 491-496, 147, British Society of Immunology.

Calderon M. et al, Specific Immunotherapy with High Dose SQ Standardized Grass Allergen Tablets was Safe and Well Tolerated; J. Investig Allergol Clin Immunol, 2006, 16(6) 338-344.

Didier A. et al, Optimal dose, efficacy, and safety of once-daily sublingual immunotherapy with a 5-grass pollen tablet for seasonal allergic rhinitis; American Academy of Allergy, Asthma & Immunology, 2007, pp. 1338-1345.

Frati F et al, Developmetn of a sublingual allergy vaccine for grass pollinosis; Drug Design, Development and Therapy, 2010 (4), pp. 99-105.

Futamura N et al, Characterization of genes for novel thaumatin-like proteins in Cryptomeria japonica; Tree Physiology, Oct. 3, 2005; (26) 51-61; Heron Publishing, Victoria, Canada.

Futamura N et al, Isolation and Characterization of cDNAs that Encode Homologs of a Pathogenesis-related Protein Allergen from Cryptomeria japonica; Biosci. Biotechnol. Biochem. 66 (11), 2495-2500, 2002.

Committee for Medicinal Products for Human Use (CHMP), Guideline on the Clinical Development of Products for Specific Immunotherapy for the Treatment of Allergic Diseases; European Medicines Agency, Nov. 20, 2008, pp. 1-13; London, UK.

Ivanciuc O et al, SDAP: database and computational tools for allergenic proteins; Nucleic Acids Research (2003) vol. 31, No. 1, pp. 359-362.

Kamdar T et al, Immunotherapy in food allergy; Immunotherapy, May 1, 2010; 2(3): 329-338.

Kleine-Tebbe J. et al, Safety of a SQ-standardized grass allergen table for sublingual immunotherapy; a randomized placebo-controlled trial; Allergy, 2006, 61: 181-184; Blackwell Munksgaard.

Lindbo, J, High-efficiency protein expression in plants from agroinfection-compatible Tobacco mosaic virus expression vectors; BMC Biotechnology, 2007 (7): 52.

Lizaso, M.T. et al, Biological standardization and maxiumum tolerated dose estimation of an Alternaria alternata allergenic extract; J. Investig Allergol Clin Immunol 2006: vol. 16 (2): 94-103.

Matsumura D et al, Detection of New Antigenic Proteins in Japanese Cedar Pollen; Biol. Pharm. Bull 2006; 29*6) 1162-1166. Pharmaceutical Society of Japan.

Namba M et al, Molecular cloning of the second major allergen, Cry j II, from Japanese cedar pollen; Federation of European Biochemical Societies (FEBS), FEBS Letters 353 (1994): 124-128.

Okubo K et al, Sublingual Immunotherapy for Japanese Cedar Pollinosis, Allergology International, 2009; 58 (2): 149-154.

Tong, JC et al, Allergen Atlas: a comprehensive knowledge center and analysis resource for allergen information; Bioinformatics, 2009, vol. 25 (7): 979-980.

Tsunematsu M et al, Effect of Cry-consensus Peptide, a Novel Recombinant Peptide for Immunotherapy of Japanese Cedar Pollinosis on an Experimental Allergic Rhinitis Model in B10.S Mice; Allergology International, 2007, 56 (4): 465-472.

Ashkenazi, M. et al, Self-Reported Compliance with Preventive Measures among Regularly Attending Pediatric Patients; Journal of Dental Education, Feb. 2007, pp. 287-295.

MacFarlane, T et al, Mouthwash Use in General Population: Results from Adult Dental Health Survey in Grampian, Scotland; Journal of Oral & Maxillofacial Research 2010 (Oct.-Dec.), vol. 1, No. 4, e2, pp. 1-9.

Sridhara et al, A Study on Antigenic and Allergenic Changes during Storage in Three Different Biological Extracts; Asian Pacific Journal of Allergy and Immunology (1992), 10: 33-38.

Reisacher et al, Oral Mucosal Immunotherapy Using a Toothpaste Delivery System for the Treatment of Allergic Rhinitis, International Journal of Pharmaceutical Compounding, Jul./Aug. 2014, vol. 18, No. 4.

Hearing Notice mailed Jul. 28, 2022 in reference to Application No. 201617013484.

First Examination Report for corresponding Indian Application No. 201617013484 dated Jul. 1, 2020.

Notification of Granting a Patent Right pertaining to corresponding Korean Patent Application No. 10-2016-7010169 dated Jan. 28, 2022.

English Translation of Japanese Office Action for corresponding JP App. No. 2019-071775 dated Mar. 30, 2020.

* cited by examiner

Cat Extract

TOOTHPASTE FOR DELIVERING ALLERGENS TO ORAL MUCOSA

PRIORITY CLAIM

This application is a continuation of U.S. application Ser. No. 16/659,875, filed Oct. 22, 2019, which is a division of U.S. application Ser. No. 15/022,249, filed Mar. 16, 2016, now U.S. Pat. No. 10,485,867, which is a national stage application under 35 U.S.C. § 371 of International Application Ser. No. PCT/US2014/056562, filed Sep. 19, 2014, which claims priority under 35 U.S.C. § 119 to U.S. Provisional Application Ser. No. 61/879,779, filed Sep. 19, 2013, and U.S. Provisional Application Ser. No. 61/879,801, filed Sep. 19, 2013, the entire disclosures of which are incorporated by reference herein.

TECHNICAL FIELD

The present invention relates to toothpaste formulations comprising allergens and/or allergenic extracts that provide controlled introduction of allergens to the immune system via the oral mucosa and to methods for treating and inhibiting the development of allergies.

BACKGROUND

Antigen-specific immunotherapy (AIT) was developed as a treatment alternative for allergic patients suffering from atopic allergies that are insufficiently controlled by treatments which focus on symptom amelioration, for example anti-histamine and corticosteroid based treatments. The aim of allergen immunotherapy (a.k.a. desensitization) is to re-educate the immune system by regular administration of doses of allergens over a sustained period of at least 3 years to a patient's immune system, thereby inducing specific long-term tolerance to those allergens. Subcutaneous immunotherapy (SCIT), refers to the introduction of these allergens by injection and has been a treatment of choice for allergic patients for more than half a century. More recently, sublingual immunotherapy (SLIT) has received considerable research and clinical attention. In general, SLIT is related to SCIT in that it refers to the delivery of the same allergens as SCIT, but is differentiated in that delivery is via an oral route rather than via subcutaneous injections. Typically SLIT-treated patients are instructed to place an allergen preparation (usually 5 drops of an aqueous solution containing allergens, commonly preserved in 50% v/v glycerin) under the tongue once per day and to hold for approximately 2 minutes before swallowing or spitting. Other emerging variations of SLIT involve dry tablets preparations containing lyophilized allergen proteins. SLIT tablets are placed under the tongue on typically a daily dosing regimen and held there for approximately two minutes. SLIT modalities provide more convenient therapeutic administrations than SCIT and possess strong safety profiles with little chance of triggering a systemic response.

Although several recent large-scale SLIT studies confirm efficacy and validate the underpinning theoretical model, the therapeutic results have not been entirely commensurate with expectations (see, e.g. Casale et al. *J Allergy Clin Immunol.* 2009 October; 124(4):665-70). Generally, predicted efficacy of SLIT is based on the observation that the oral mucosa appears particularly primed in mammals for development of allergenic tolerance and possesses specialized cells that function to achieve this. However, a key to successful AIT is achieving a high level of patient compliance with the conventional administration schedule of the SCIT or SLIT treatment protocols. A typical exemplary protocol includes daily administration for 3-4 years for SLIT, and weekly or bi-weekly doctor-administered injections for 3-4 years for SCIT. Many studies have demonstrated that, in practice, significant numbers of patients fail to comply with AIT regimens for the full treatment course. The reasons for non-compliance vary between the various SCIT and SLIT regimens, but overall patient convenience is most often cited as the common driver for low compliance. The result is an elevated risk of unsatisfactory or poor treatment outcomes for those patients.

Further, recent studies suggest that certain regions of the oral mucosa are more amenable to AIT than others, and the selection of the sub-lingual region as a vaccine target related more to established existence of sub-lingual delivery forms than to differential efficacy with respect to regions of the oral mucosa. In particular, the highest number of T cells was located in the oral vestibular/buccal region (VBR) and significantly higher TGF-β1 mRNA expression was observed in the VBR compared with the sublingual region (SLR). Moreover, expression of toll-like receptor (TLR) 2 and TLR4 was highest in VBR with significant expression on dendritic cells in the vestibular mucosa. (Allam J P et al. Tolerogenic T cells, Th1/Th17 cytokines and TLR2/TLR4 expressing dendritic cells predominate the microenvironment within distinct oral mucosal sites. Allergy 2011, 66:532-539)

Other modes of delivering AIT via the oral mucosa have been contemplated that are more convenient and patient-friendly, and which also have a therapeutic advantage of reaching other tissue regions of the oral mucosa in addition to sub-lingual regions. It has recently been suggested that combining allergens with commonly used oral products such as toothpaste, chewing gum, and mouthwash may provide a means for delivery and sufficiently sustained contact of the active with target tissue that results in higher compliance. This relatively new mode of AIT delivery, also known as "oral mucosal immunotherapy" (OMIT), is receiving increased interest in the allergy community. In contrast to SLIT, OMIT permits the selected allergens to be administered regularly as part of the subject's ordinary habits/routines. For example, if admixed with toothpaste, allergen exposure occurs nearly transparently to the subject during the subject's already established typically twice daily tooth brushing routine. Hence, compliance may be greatly increased.

OMIT via oral personal care products further exploits advances in the allergy acquisition and control clinical sciences suggesting that contacting allergens with areas of the oral mucosa other than the sub-lingual mucosa may be more effective in achieving a de-sensitization benefit. For example, in effectuating OMIT via a toothpaste/toothbrushing regimen, allergens will necessarily contact a much broader surface of the oral mucosal tissue during daily tooth-brushing than via SLIT, wherein exposure is confined specifically to the area under the tongue. Publication WO/2011/137420 describes the concept and benefits of OMIT and in particular OMIT toothpaste, the disclosure of which is incorporated herein in its entirety by this reference. Further, that mechanical result of "brushing" in particular may irritate and prime the outer cells of the oral mucosa for a faster desirable interaction with target mast cells.

For consumer satisfaction, toothpaste products are generally formulated to possess certain sensory and physical properties to which the consumer is accustomed. These properties provide a toothpaste product having an appealing taste, satisfactory cleansing effect, excellent mouth feel, physical stability, and sufficient rinsability. Toothpaste compositions with acceptable physical stability do not readily harden on the shelf and do not exhibit phase separation resulting in water or flavor separation. The appearance of the paste as it comes out of the dispenser is also considered an important feature. Consumer studies suggest that the toothpaste should appear smooth and have a pleasant sheen or glossy appearance.

Although the concept of an OMIT toothpaste formulation has been posited and at least suggests therapeutic advantage over traditional SLIT, a formulation providing the desirable cosmetic product and efficacy profile has proven difficult to achieve. A desirable OMIT toothpaste formulation should be as similar to the non-OMIT toothpastes familiar to consumers as possible. Generally, an OMIT toothpaste should have the following properties: (1) homogeneous dispersion of allergen throughout the toothpaste (2) immunologic properties of the allergens conserved over a time frame reasonably commensurate with expectations of toothpaste product life, and (3) a consumer phenomenological experience profile of appearance, flavor, consistency, texture, and mouth feel that is similar to known products and encourages daily use. However, initial attempts at formulating a suitable toothpaste with allergens or allergen extract suffered from severe degradation of consistency, appearance, and texture immediately or within 2-3 days. Ilene, there remains a need for consumer-acceptable OMIT toothpaste formulations suitable for providing a variety of allergens efficaciously via OMIT treatment modalities.

SUMMARY OF THE INVENTION

Accordingly, the present invention provides pro-toothpaste formulations and OMIT toothpaste formulations which overcome the deficiencies in the art, and methods employing the toothpastes for habituating an immune response to allergens by exploiting existing consumer oral hygiene habits. The instant invention provides compositions and methods for formulating compositions of Pro-toothpaste that are suitable for mixture with a defined volume of allergens to make a toothpaste appealing to consumers and that provide OMIT during daily tooth brushing regimens. In very specific embodiments, an OMIT toothpaste comprises a food introduction technology (FIT) toothpaste adapted for introduction of food allergens to children generally below the age of 6.

One embodiment provides pro-toothpaste compositions formulated to be combinable with an allergen or allergen extract suspended in a solution comprising a sugar alcohol, the pre-toothpaste composition comprising: a sugar alcohol selected to correspond to a sugar alcohol present in the suspension solution, and a viscosity modifier. Embodiments of toothpaste compositions formulated by combining a pro-toothpaste according to the invention with an allergen or allergen extract suspended in a solution comprising a sugar alcohol, wherein the toothpaste composition comprises between about 25% and about 75% sugar alcohol by volume and about 20% silica-based viscosity modifier by weight, are also provided.

Other embodiments are directed to oral mucosal therapy kits comprising at least one vial of pro-toothpaste according to embodiments of the invention, and at least one vial of solution comprising at least one allergen or allergen extract. In some embodiments, at least one allergen or allergen extract is selected to accommodate a food introduction technology regimen.

According to another embodiment, methods for formulating a toothpaste suitable for oral mucosal therapy are provided. The methods comprise: providing a first volume of solution comprising an allergen or allergen extract and a concentration of sugar alcohol; formulating a second volume of pro-toothpaste comprising a reduced concentration of vehicle and an increased concentration of thickener when compared to a conventional toothpaste, the vehicle comprising a sugar alcohol corresponding to the sugar alcohol of the first volume in a concentration substantially corresponding to the concentration of sugar alcohol of the first volume, the first and second volumes being combinable in a ratio such that a concentration of sugar alcohol in the combined volume is between about 45% and 55% by volume, and mixing the first volume and second volume in the ratio.

Other method embodiments provide methods for reducing an immune response to an allergen in a subject. The methods comprise delivering an amount of one or more allergens to a target area of the oral mucosa of the subject by contacting the target area of the oral mucosa with a toothpaste formulation according to the invention at least once daily. In certain aspects, the methods accommodate a food introduction technology regimen, wherein the subject is a human between the ages of 4 months and 6 years.

Another embodiment provides methods for diagnosing propensity to developing a food allergy in a human between the ages of 4 months and six years. The methods comprise (a) formulating a toothpaste according to claim 29 to include an allergenic protein from one food product and (b) contacting an area of the human's oral mucosa with the toothpaste formulated in step (a) in a daily regimen for a time frame; (c) monitoring for symptoms of an immune response in the oral mucosa during or after the time frame; (d) repeating steps (a), (b) and (c) until practiced with at least 1, 2, 3, up to 8 or more toothpaste formulations, one for each independent food product, and diagnosing a propensity to developing an allergy to a food product where symptoms of an immune response are observed in (c).

These and other embodiments will be more fully understood by reference to the Figures and Detailed description below, although it should be noted that Figures and Examples are for illustrative purposes and should not be construed as limiting the full scope of the subject matter as defined by the claims appended hereto. All references (e.g., printed publications such as books, papers, patents, patent applications, catalogs, databases) are incorporated herein by reference. In the event of a conflict or inconsistency, the present specification, as modified by any amendments thereto, shall control.

DETAILED DESCRIPTION

Figure 1:
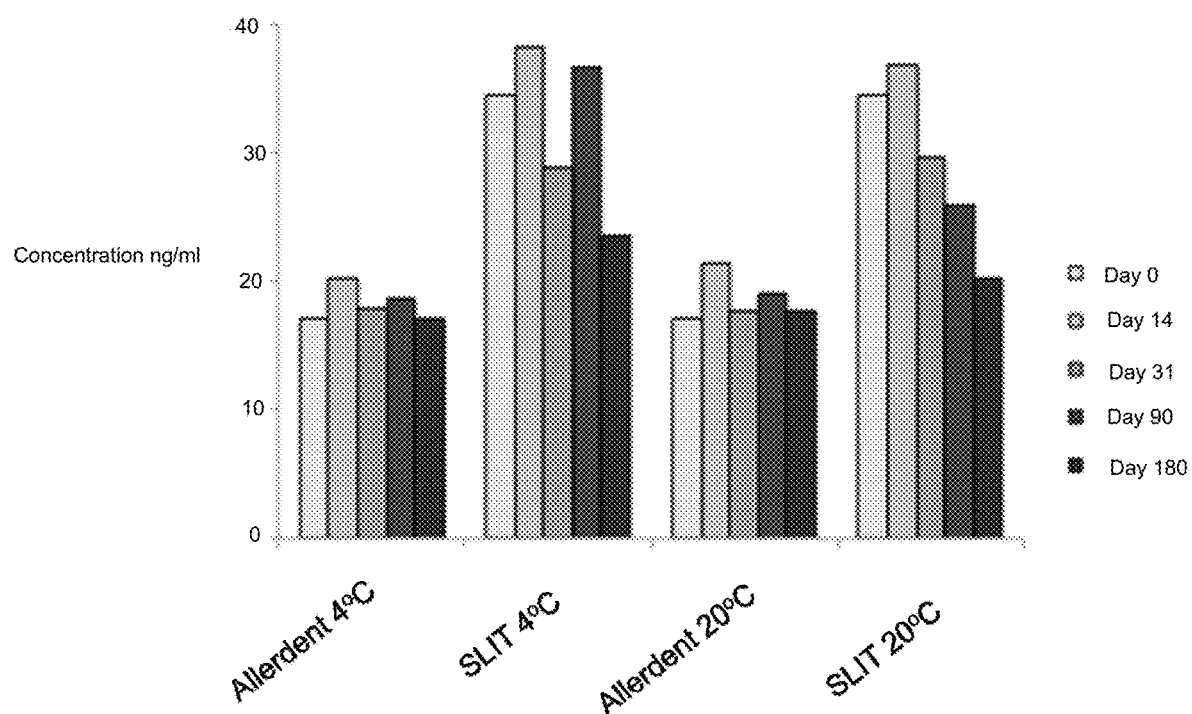
FIG. 1. A bar graph comparing stability of dust mite allergen extract Der 1 f over 180 days when formulated into a toothpaste according to the invention versus Der 1 f extract in glycerol suspension.

The following description provides embodiments described in detail sufficient to enable those skilled in the art to practice the invention, and it is to be understood that other embodiments not specifically disclosed may be utilized and that changes may be made without departing from the reasonably contemplated scope of the present invention. The following exemplary disclosures should not be taken as limiting the proprietary scope as defined by the appended claims.

Unless the context indicates otherwise, in the specification and claims, the terms abrasive, polishing agent, humectant, binder, thickener, surfactant, surface active agent, flavoring, flavoring agent, sweetener, sweetening agent, buffer, preservative, allergen, allergen extract, antigen, and similar terms also include mixtures of like materials. Unless otherwise specified, all percentages are percentages by weight. These terms should be construed to comport with their ordinary meaning in the art. A "Pro-toothpaste" as used herein is a toothpaste comprising an ingredient profile substantially similar to conventional toothpaste compositions; however certain ingredients may be eliminated and vehicle is reduced to provide a composition that mixes with one or more allergens and/or allergen extracts to provide an end-product toothpaste with desired stability, efficacy and consumer profiles are achieved upon combination.

Toothpaste, occasionally also referred to as dentifrice, is commonly used with a toothbrush as an accessory to clean and maintain the aesthetics and health of teeth. Toothpaste is used to promote oral hygiene: it serves as an abrasive that aids in removing the dental plaque and food from the teeth, assists in suppressing halitosis, and delivers active ingredients (mainly fluoride) to help prevent tooth and gum disease (gingivitis). The present investigators have developed Pro-toothpaste compositions which may be combined with allergens suspended in particular solutions to form a suitable consumer toothpaste product such that the allergens are brought into contact with the oral mucosa during toothbrushing. Thus administration of AIT to treat allergic conditions can be effectuated during the ritual of daily dental care as "oral mucosal immunotherapy" (OMIT). Publication WO/2011/137420 has described the concept of using toothpaste as a novel delivery modality of AIT, the entire disclosure of which is incorporated herein in its entirety by this reference.

For consumer satisfaction, toothpaste compositions should possess certain acceptable physical properties to which the consumer is accustomed. These properties provide toothpaste that has appealing taste, has good cleansing effect, is easy to rinse, has excellent mouth feel, and has physical stability. Moreover, toothpaste compositions must possess an acceptable physical stability profile such that they do not readily harden on the shelf and do not exhibit phase separation such as water or flavor separation. The appearance of the paste as it comes out of the dispenser is also considered important. Studies show that consumers prefer a toothpaste that appear smooth and has a pleasant sheen or glossy appearance.

Embodiments of the instant invention provide Pro-toothpaste compositions, and methods of formulating such compositions, that are suitable for combining with allergens, preferably suspended in aqueous solution or 50% v/v glycerin. Other embodiments provide the constituted toothpaste product, referred to herein as "OMIT toothpaste," that possesses stability, efficacy and consumer characteristics substantially similar to those of conventional toothpastes. Other embodiments are directed to kits comprising Pro-toothpaste contained separately from one or more compositions comprising allergen or allergen extract. According to more specific embodiments, a kit may comprise one or more optional items such as mixing vessels, metered dose-dispensers, and a toothbrush. In very specific embodiments the toothbrush is adapted to optimize exposure of target oral mucosa cells to allergen, for example, gum massaging or stimulating extensions. Other embodiments provide methods for preventing, treating, diagnosing and managing allergic conditions in both humans and other mammals susceptible to development of allergy.

A Pro-toothpaste is a portion of the toothpaste product comprising typical ingredients of a toothpaste, however with one or more typical ingredients eliminated, replaced, or reduced to accommodate mixture of the Pro-toothpaste with a second portion comprising allergen or allergen extract. For example, a typical vehicle may comprise humectant and water. According to a specific embodiment, formulating the composition of the Pro-toothpaste comprises retaining the amounts of binder, surface active agent, and abrasive in a typical toothpaste composition, while decreasing the total percentage of vehicle (water and/or humectant) by an amount that corresponds to the predetermined volume of allergens to be added to the Pro-OMIT toothpaste, such that the Pro-toothpaste is concentrated. In one illustrative example, allergens suspended in aqueous or 50% v/v glycerin solution are combined with a Pro-toothpaste such that the toothpaste may be reconstituted by, for example, a clinician, a pharmacist or a consumer, to a usable form as a finished allergen-containing OMIT toothpaste product.

One embodiment is directed to a pro-toothpaste composition formulated to be combinable with an allergen or allergen extract suspended in a solution comprising a sugar alcohol, the pre-toothpaste composition comprising: a sugar alcohol selected to correspond to a sugar alcohol present in the suspension solution, and a viscosity modifier. In specific embodiments the sugar alcohol comprises glycerol and the viscosity modifier comprises a silica-based viscosity modifier in an amount of between about 12% and about 30% by weight, and according to more specific embodiments, the composition comprises between about 40% and 60% by weight glycerol. In very specific embodiments, the pro-toothpaste composition comprises about 50% by volume glycerol and about 20% silica-based viscosity modifier by weight.

In other embodiments, the method of formulating the composition of OMIT toothpaste comprises retaining the amounts/relative percentages of binder, surface active agent, abrasive, and humectant in a typical toothpaste composition, while decreasing the percentage of water by an amount that corresponds to the predetermined volume of allergens to be added to the Pro-toothpaste.

In other embodiments, formulating the composition of the OMIT toothpaste comprises decreasing the total percentage of vehicle (water and/or humectant) in a typical toothpaste composition by about 10%, or about 15%, or about 20%, or about 25% to form the Pro-toothpaste portion. According to other embodiments, the predetermined volume of allergens to be combined with a Pro-toothpaste composition may correspond to a volume ratio of about 2 parts Pro-toothpaste to about 1 part allergen, or 3 parts Pro-toothpaste to about 1 part allergen, or about 4 parts Pro-toothpaste to about 1 part allergen, or about 5 parts Pro-toothpaste to about 1 part allergen, or about 6 parts Pro-toothpaste to about 1 part allergen.

In more specific embodiments, formulating the composition of the Pro-toothpaste comprises retaining the relative amounts of binder, surface active agent, and abrasive, and other ingredients in a typical toothpaste composition, while decreasing the percentage of vehicle (water and/or humectant) by about 20%, wherein the predetermined volume of allergens to be added to the Pro-toothpaste composition is in a volume ratio of about 4 parts Pro-toothpaste to about 1 part allergen.

Compositions of Pro-toothpaste are provided. In one embodiment, the Pro-toothpaste comprises a binder; a surface active agent; an abrasive; a humectant; and water; in which;
(1) the binder comprises about 10%-22% (w/w),
(2) the surface active agent comprises about 1.0%-2.0% (w/w),
(3) the abrasive comprises about 5%-10% (w/w),
(4) the humectant comprises 40%-55% (w/w),
(5) the water comprises about 18%-25% (w/w),
and which optionally comprises a sweetener; a preservative; a flavoring agent; an opacifier and/or coloring agent, and an anti-caries agent; in which
(6) the sweetener comprises about 0.2%-0.4% (w/w),
(7) the preservative comprises about 1.5%-3% (w/w),
(8) the flavoring agent comprises about 0.5%-1.5% (w/w),
(9) the opacifier and/or coloring agent comprises about 0.1%-0.2% (w/w), and
(10) the anti-caries agent comprises about 0.2%-0.5% (w/w).

In other embodiments of the invention, the formulation of Pro-toothpaste comprises a binder; a surface active agent; an abrasive; a humectant; water; a sweetener; a preservative; a flavoring agent; an opacifier or coloring agent, and an anti-cavity agent; in which;
(1) the binder comprises about 0.35%-0.45% (w/w) Carbomer 940™ or similar binding agent; about 0.75%-1.0% (w/w) sodium carboxymethylcellulose (CMC) or similar binding agent; and about 10%-20% (w/w) Zeodent 153™ or similar silica thickener,
(2) the surface active agent comprises about 1.0%-2.0% (w/w) sodium lauryl sulfate (SLS) or other similar agent,
(3) the abrasive comprises about 5.0%-10.0% (w/w) Zeodent 113™ or other similar abrasive,
(4) the humectant comprises about 40%-55% (w/w) polyol, such as glycerin or sorbitol (in 70% w/v solution), or other humectant
(5) the water comprises about 18%-25% (w/w),
(6) the sweetener comprises about 0.2%-0.4% (w/w) sodium saccharine, or other similar sweetener
(7) the preservative comprises about 1.0%-2.0% (w/w) sodium phosphate tribasic (Na3PO4), and about 0.5%-1.0% sodium phosphate monobasic (NaH2PO4), or other similar preservative,
(8) the flavoring agent comprises about 0.1%-1.5% (w/w) of natural peppermint oil or other similar flavor agent,
(9) the opacifier and/or coloring agent comprises about 0.1%-0.2% (w/w) of titanium dioxide and/or other opacifier or coloring agent, and
(10) the anti-cavity agent comprises about 0.2%-0.5% (w/w) sodium fluoride (NaF) or other similar anti-cavity agent.

In a specific embodiment of the invention, the Pro-toothpaste formulation comprises a binder; a surface active agent; an abrasive; a humectant; water; a sweetener; a preservative; a flavoring agent; an opacifier agent, and an anti-cavity agent; in which;
(1) the binder comprises about 0.43% (w/w) Carbomer 940™; about 0.935% (w/w) sodium carboxymethylcellulose (CMC); and about 12.3% (w/w) Zeodent 153™
(2) the surface active agent comprises about 1.41% (w/w) sodium lauryl sulfate (SLS) or other similar agent,
(3) the abrasive comprises about 6.15% (w/w) Zeodent 113™ or other similar abrasive,
(4) the humectant comprises about 53.1% (w/w) glycerin,
(5) the water comprises about 22.9% (w/w),
(6) the sweetener comprises about 0.246% (w/w) sodium saccharine,
(7) the preservative comprises about 1.23% (w/w) sodium phosphate tribasic ($Na_3PO_4$) and about 0.614% (w/w) sodium phosphate monobasic ($NaH_2PO_4$),
(8) the flavoring agent comprises about 0.254% (w/w) natural peppermint oil,
(9) the opacifier agent comprises about 0.123% (w/w) titanium dioxide, and
(10) the anti-cavity agent comprises about 0.254% (w/w) sodium fluoride (NaF).

According to some embodiments of the invention, Pro-toothpaste compositions are formulated to comprise reduced percentages of, and/or to eliminate particular conventional toothpaste ingredients. Consequently the concentration of thickening agents and viscosity and/or rheology modifiers is increased. The vehicle of a toothpaste composition typically comprises water and/or humectant. The instantly inventive OMIT toothpaste product compositions are formulated from a "base" toothpaste composition referred to herein as a Pro-toothpaste. Following manufacture of a Pro-toothpaste, it is intended that one or more allergens can be added to, and homogeneously mixed with, the Pro-toothpaste (i.e., by an appropriate agent such as a drug manufacturer, a compounding pharmacy, an allergy clinician, etc, or in accordance with other embodiments by a consumer or other party at the site of intended use). Mixing in accordance with embodiments of the invention comprises generally hand-mixing or low-speed mixing without the use of shearing elements and without imparting a substantial increase in energy to the formulation resulting in a temperature increase.

Allergens in accordance with specific embodiments are suspended in a water and/or glycerin solution such that when the solution is combined with the Pro-toothpaste, the allergen solution mixes readily and homogeneously with vehicle components to provide an OMIT toothpaste product. More specifically, the addition of a defined volume of allergen solution will complete an OMIT toothpaste composition, resulting in texture, consistency, mouth-feel, and other important properties of the composition being comparable to those of a known toothpaste products usable for daily dental care.

In specific embodiments of the invention, Pro-toothpaste compositions are mixed with allergens suspended in aqueous and/or glycerin solutions in a specific volume ratio of 4 parts Pro-toothpaste to 1 part allergen solution to form an OMIT toothpaste. For clarity, this means 2 ml of allergen solution is added to every 8 ml of Pro-toothpaste to give approximately 10 ml of finalized OMIT toothpaste. The formulation of 8 ml of the Pro-toothpaste comprises percentage weight amounts of ingredients, such as an abrasive or polishing agent, a binder, a surface active agent, that are intended for 10 ml of final OMIT toothpaste, but about 20% less toothpaste vehicle volume. In other specific embodiments, volume ratios between Pro-toothpaste and allergen solutions may be about 2 parts Pro-toothpaste to about 1 part allergen solution, or 3 parts Pro-toothpaste to about 1 part allergen solution, or about 5 parts Pro-toothpaste to about 1 part allergen solution, or about 6 parts Pro-toothpaste to about 1 part allergen solution.

Conventional toothpastes are widely available to consumers as over-the-counter products under many well-known brand names such as Colgate®, Crest®, Aim™, Oral B®, Aqua-Fresh®, and Close-up®. Although the formulations of commercially available typical toothpaste differ, they nonetheless comprise similar classes of ingredients. Typical commercial toothpaste ingredients include one or more of an abrasive or polishing agent, humectant, binder, surface active agent, water, and, optionally, other materials that are typical components of toothpaste compositions, such as flavors, coloring agents, sweeteners, preservatives, and, optionally, agents that prevent caries, tooth decay, and gum disease. The humectant and water ingredients of are often referred to collectively as the toothpaste "vehicle". Specific ingredients may also vary from country to country according to local legislation on use of ingredients.

The present investigators surprisingly discovered that although ingredient class constituents of conventional toothpaste products are very similar, even upon reduction in vehicle volume to accommodate extract suspension composition volume, some reduced-vehicle toothpaste products combined with allergen or allergen extract to form a suitable product, while others combined to form a product that exhibited unacceptable texture, consistency, stability, and mouth feel. Even more surprisingly, it was discovered that very specific formulation adjustments could provide a "Pro-toothpaste" capable of readily mixing with allergens suspended in water or glycerin to provide acceptable OMIT toothpaste products having an acceptable stability, final consistency, texture, and other important properties. In particular, stability of allergens is enhanced when the sugar alcohol of the allergen extraction suspension corresponds to a sugar alcohol humectant present in the Pro-toothpaste formulation such as illustrated in Example 5, both with respect to specific sugar alcohol and with respect to weight percentage of each formulation.

In some embodiments, an OMIT toothpaste composition of the invention is formulated to provide a product that is an extrudable, creamy material after combination with allergens. The binder, or thickener, builds viscosity, provides desirable consistency and thixotropy, and prevents separation of the ingredients during storage and use. Suitable thickeners include cellulose derivatives ("cellulose gums") such as carboxymethyl cellulose (CMC), methyl cellulose, hydroxyethyl cellulose, hydroxypropyl methyl cellulose, and mixtures thereof; polyvinyl pyrrolidone; xanthan; carrageenans such as iota-carrageenan, kappa-carrageenan, kappa2-carrageenan, lambda-carrageenan, and mixtures thereof; guar gum; gum karaya; gum arabic; gum tragacanth; and mixtures thereof. Other suitable thickeners include Carbomer 910, Carbomer 934, Carbomer 940, and Carbomer 980 and similar polymers of acrylic acid which are cross-linked with polyalcohol allyl ethers. Hydrated silica and colloidal silica may be used as thickeners. Silica thickeners suitable for invention embodiments, such as Zeodent 153®, Zeodent 163®, and Zeodent 165®, (J.M. Huber Co., Edison, N.J. USA) are disclosed, for example, in Niemi, U.S. Pat. No. 6,342,205, the entire disclosure of which is incorporated herein by this reference). The present investigators surprisingly found that Pro-toothpaste formulations comprising one or more silica thickeners combine with allergen extract suspended in solutions comprising glycerol to provide an enhanced stability effect.

The toothpaste compositions of the invention may also comprise an abrasive, sometimes referred to as a polishing agent. Suitable abrasives, or polishing agents, include finely divided water-insoluble powdered materials having no or very low water solubility, typically having a particle size of about 1 to 40 microns in diameter, more typically about 2 to 20 microns in diameter, with normal particle size distributions. These materials have polishing activity without being overly abrasive. Typical abrasives include: calcium-based polishing agents, such as dicalcium phosphate dihydrate (generally known as dicalcium phosphate), tricalcium phosphate, calcium carbonate (such as limestone, natural chalk, or precipitated chalk), calcium pyrophosphate, calcium silicate, and calcium aluminate; magnesium carbonate; magnesium phosphate; sodium metaphosphate; amorphous silica; crystalline silica; precipitated silica such as Zeodent 1130, Zeodent 115®, Zeodent 124®, or Zeodent 623® (J.M. Huber Co., Edison, N.J. USA); complex aluminosilicate; aluminum hydroxide; aluminosilicates, bentonite, talc, aluminum oxide, silica xerogels, and mixtures thereof. More typical abrasives are dicalcium phosphate, calcium carbonate, and silica.

According to certain aspects, a vehicle component comprises water and a humectant. The total vehicle volume of a Pro-toothpaste [water+humectant] may be varied over conventional toothpaste compositions in terms of its percentage composition (w/w) in order to adjust for addition of allergens. Allergens may be suspended in a solution formulated to readily combine with the vehicle aspect of a Pro-toothpaste. In specific embodiments the allergen solutions comprise aqueous and/or glycerin in percentage amounts substantially similar, to a vehicle component of a Pro-toothpaste. Commercially available allergens vary from country to country based on regulatory scheme and other legal concerns. Typical commercially available allergen extract solutions comprise allergen suspended in aqueous or glycerin solutions. In very specific embodiments an allergen extract solution comprises at least about 50% glycerin v/v, and in very specific embodiments an allergen extract comprises about 50% glycerin v/v.

A humectant provides mouth feel and also prevents a toothpaste composition from drying out. Toothpastes are typically formulated with humectants comprising polyols of three to six carbons in which each carbon is hydroxylated, and mixtures thereof. Specific non-limiting examples include glycerin (glycerol), sorbitol, polyethylene glycol, polyoxyethylene glycol, mannitol, xylitol, and other sugar alcohols. It should be appreciated that since glycerin, sorbitol, and xylitol also have sweetening properties, their inclusion in toothpaste compositions can limit the need to include additional sweeteners, such as sodium saccharine. According to embodiments of the invention, Pro-toothpaste is formulated with glycerol as the sole or predominant sugar alcohol.

Toothpaste compositions of the invention may also comprise a surface active agent, often with surfactant properties, to emulsify or otherwise uniformly disperse toothpaste components. The surface active agents are typically anionic or nonionic surface active agents, or mixtures thereof. Examples of suitable surface active agents include water-soluble salts of higher fatty acid monoglyceride monosulfates; higher alkyl sulfates; higher alkyl aryl sulfonates; higher alkyl sulfoacetates; higher fatty acid esters of 1,2 dihydroxy propane sulfonate; substantially saturated higher aliphatic acyl amides of lower aliphatic amino carboxylic acid compounds, such as those having 12 to 16 carbon atoms in the fatty acid, alkyl or acyl radicals; higher olefin sulfonates, higher alkyl poly-lower alkoxy (of 3 to 100 alkoxy groups) sulfates, and fatty acid soaps. Examples of these anionic surface active agents include sodium lauryl sulfate (SLS), sodium hydrogenated coconut oil fatty acids monoglyceride monosulfate, sodium dodecyl benzene sulfonate, sodium lauryl sulfoacetates, sodium N-lauryl sarcosinate, and sodium cocate. Suitable types of nonionic surface active agents include chains of lower alkylene oxides such as ethylene oxide and propylene oxide. A preferred surface active agent for invention embodiments is sodium lauryl sulfate (SLS).

The toothpaste compositions of the invention may comprise a number of other ingredients. Agents that provide therapeutic or cosmetic benefits may be present, such as enamel hardening agents, tartar control agents, whitening agents, and antibacterial agents. One or more sweeteners and flavorings may be added for consumer satisfaction. Other materials that are conventional components of toothpaste compositions, such as opacifers and colorants, may also be present.

Examples of flavorings (flavors, flavoring materials, or flavoring agents) include: menthol; carvone; anethole; methyl salicylate; and the oils of spearmint, peppermint, wintergreen, sassafras, clove, sage, eucalyptus, marjoram, cinnamon, lemon, lime, grapefruit, kumquat, tangerine, and orange. Preferred flavoring oils, such as peppermint oil, may be extracted and purified from natural sources or synthesized.

Examples of sweeteners (sweetening agents) include sucrose, lactose, maltose, sorbitol, xylitol, sodium cyclamate, perillartine, L-aspartyl-L-phenylalanine methyl ester (aspartame), and saccharine. Specific embodiments comprise saccharine, which may be included as sodium saccharine. According to certain embodiments of the invention, an amount of artificial sweetener typical in conventional toothpaste formulations may be reduced by reliance predominantly or solely on glycerol as a humectant.

Pyrophosphate salts having anti-tartar efficacy such as a dialkali or tetra-alkali metal pyrophosphate salts such as $Na_4P_2O_7$ (TSPP), $K_4P_2O_7$, $Na_2K_2P_2O_7$, $Na_2K_2H_2O_7$, and $K_2H_2P_2O_7$, long chain polyphosphates such as sodium hexametaphosphate, and cyclic phosphates such as sodium trimetaphosphate may be present in the toothpaste composition.

Examples of hardening agents are fluoride salts such as sodium fluoride, potassium fluoride, calcium fluoride, zinc fluoride, stannous fluoride, zinc ammonium fluoride, sodium monofluorophosphate, potassium monofluorophosphate, and laurylamine hydrofluoride.

Preservatives or stabilizers may also be included in the toothpaste compositions of the invention. Especially useful are non-cationic antibacterial agents that are based on phenolic and bisphenolic compounds, halogenated diphenyl ether, benzoate esters and carbanilides, such as sodium benzoate; 4-chlorophenol, 2,2'-trichloro-2-hydroxy-diphenyl ether (triclosan); esters of p-hydroxybenzoic acid, especially the methyl, ethyl (ethyl parasept), propyl (propyl parasept), butyl (butyl parasept), and benzyl esters; 3,4,4'-trichlorocarbanalide and 3,3',4-trichlorocarbanilide. A preferred antimicrobial agent is triclosan. Nonionic antimicrobial agents such as sesquiterpene alcohols such as merolidol and bisabolol are also useful. Preferred preservatives of the invention are sodium phosphate monobasic ($NaH_2PO_4$) and sodium phosphate tribasic ($Na_3PO_4$) and similar agents, which additionally have useful pH buffering properties.

Whitening agents may be present in the toothpaste composition. Useful whitening agents are oxidizing agents such as calcium peroxide, urea peroxide, peracetic acid, and sodium percarbonate.

The toothpaste composition may also comprise other ingredients that are conventional components of toothpaste compositions, including, for example, opacifier agents, such as titanium dioxide, may be added to make the toothpaste opaque or to increase its opacity. Other ingredients may be orally acceptable colorants such beta-carotene, chlorophyllin, FD&C Yellow #5, FD&C Yellow #6, FD&C Blue #2, FD&C Red #4, FD&C Green #6, FD&C Yellow #10, FD&C Red #40, D&C Green #5, D&C Red #30 lake, and FD&C Blue #1 lake; healing agents, such as rose-seed oil; chelating/sequestering agents, such as citrates; vitamins, such as vitamin C and vitamin E; amino acids; proteins; antibiotics; anti-enzymes; enzymes; pH control agents (buffers); antioxidants; and preservatives.

Allergens according to the invention may include any agent which triggers a measurable immune response. For example, an allergen may include any agent which triggers measurable production of IgE in at least some individuals exposed to the allergen (e.g., at least some atopic individuals). In many embodiments, an allergen comprises an agent that triggers an allergic reaction (type I hypersensitivity reaction) in at least some individuals exposed to the allergen (e.g., at least some atopic individuals). In some embodiments of the invention, the allergen is an air-borne allergen. Typically, the main route by which subject are exposed to such allergens is though inhalation. In some embodiments of the invention, the allergen is one to which subjects are mainly exposed by skin contact with the allergen. In some embodiments of the invention, the allergen is one to which subjects are mainly exposed by ingesting the allergen. In some embodiments of the invention, the allergen is one to which subjects are mainly exposed by injection.

Exemplary allergens according to the invention include allergens of plant, animal or fungal origin. Plant allergens include pollen, sap, leaves and plant toxins, while examples of fungal allergens include polypeptides produced by molds, *Aspergillus* and others. Animal allergens include polypeptides produced by insects, fecal allergens of dust mites and mammals, in particular of cats, and animal keratinacious dander. Specific examples include ragweed pollen, dust mite and dust mite excrement, animal dander and mold. Other examples of allergens include food allergens, various insect venoms, and a number of industrial chemicals and pharmaceutical agents (e.g., penicillins, cephalosporins, cancer chemotherapy drugs, etc). An "allergen" as used herein may refer to one or more allergens, and may refer to any combination of allergens within and/or between the major classes of animal, plant, and fungi/mold. "Food allergens," in particular, may be from any class or any combination of classes.

Plant pollens are major sources of airborne allergy throughout many areas of the world. In some embodiments of the invention, an allergen comprises grass pollen. Grasses, as used herein, include members of the family Poaccac (sometimes termed "true grasses"), rushes (Juncaccac) and sedges (Cyperaceae). Grasses are distributed widely throughout many regions of the world, with different species having variable importance in different geographical areas. For example, grass species common in at least some regions of Europe and/or the US include *Dactylis glomerata* (orchard grass), *Poa pratensis* (Kentucky bluegrass), *Lolium perenne* (ryegrass), *Anthoxantum odoratum* (sweet vernal), *Phleum pratense* (timothy), *Festuca eliator* (meadow fescue), *Agrostis alba* (redtop), and *Cynodon dactylon* (Bermuda grass). Grass allergens include, e.g., Poa a 1 (UniProt™ acc. no. Q9ZP03) and Poa p 5 (UniProt™ acc. no. Q9FPR0). In some embodiments of the invention, an allergen is from a grass within the *Dactylis, Poa, Lolium, Anthoxantum, Phleum, Festuca, Agrostisi* or *Cynodon* genus, e.g., any of the afore-mentioned species. For example, an allergen can comprise a Poa a, Poa p, or Phi p protein.

In some embodiments of the invention, a plant allergen is pollen (or an extract or component thereof) of a tree or shrub that is a member of the Cupressaceae family. It should be noted that the Cupressaceae (cypress) family includes a number of species whose common name includes the word "cedar". In some embodiments, the allergen is pollen from a species in the subfamily Cupressoideae, e.g., a member of the genus *Chamaecyparis* or *Juniperus* ("juniper"). In some embodiments, the allergen is pollen from *Cryptomeria japonica* (family Cupressaceae, subfamily Taxodioidca), commonly referred to as Sugi or Japanese cedar.

One of ordinary skill in the art will appreciate that, in general, particular allergenic molecules (e.g., particular proteins) within allergens such as pollens, dusts, danders, molds, foods, etc, are responsible for triggering the allergic reaction. It is common to refer both to the particular allergenic molecules (e.g., particular proteins) and the materials in which they are found as "allergens", and that convention is use herein. Thus, reference to an "allergen" encompasses allergens in natural forms such as pollens, dusts, danders, molds, foods, or venoms, extracts of such natural forms of allergens, and allergenic molecules (e.g., particular proteins) that are at least partially purified or substantially purified or isolated from natural sources or produced using, e.g., recombinant DNA technology.

Common sources of food allergens include peanuts, tree nuts, eggs, milk, shellfish (e.g., shrimp, crab), fish, wheat, soy and their derivatives. In very specific embodiments of the invention, allergens and/or allergen extracts are selected as part of a Food Introduction Technology (FIT) regimen, in particular for children. In certain aspects, an OMIT toothpaste comprises a FIT toothpaste.

The Center for Disease Control and Prevention estimates the prevalence of food allergy (FA) in children less than 18 years of age in the United States to be approximately 4-8%, with an estimated 18% increase from 1997-2007. These concerns are also relevant for adults, with an estimated 4% prevalence of food allergies. Reactions to foods may range from mild oral cavity itching to life-threatening anaphylactic reactions, which are responsible for approximately 200 deaths per year in the (IS.

Previous recommendations for the introduction of solid foods were avoiding milk for the first year of life, eggs until the age of 2 and not introducing tree nuts, peanuts, fish or shellfish until the age of 3. However, in 2008 the American Academy of Pediatrics (AAP) adjusted their position to state that there was no reason to withhold any solid foods beyond the age of 4-6 months. In 2010, the National Institute of Allergy and Infectious Diseases (NIAID) published guidelines concerning the diagnosis and management of FA stating, "The introduction of solid foods should not be delayed beyond 4-6 months of age" [NIAID Food Allergy Guidelines 2010]. In addition, they reported that restricting the maternal diet during pregnancy or lactation was not successful for the purposes of preventing FA in normal or high-risk infants, and in fact may be contributive.

Food allergies are most likely to occur during the first few years of life in genetically-susceptible individuals. While food allergies are often outgrown by later childhood, exposure to certain foods may initiate a cascade of inflammatory conditions, known as the "atopic march", typically starting with atopic dermatitis (AD) and allergic rhinitis (AR), then leading to asthma and other allergic co-morbidities such as sinusitis and ear disease. Inferential evidence for early childhood as a critical period for exposure sufficient to de-sensitize an immune response abounds. With delayed introduction of solid foods, Australia saw a 5-fold increase in food anaphylaxis in children under 4 years of age. Recommendations to delay ingestion of peanuts in the UK and North America have resulted in a doubling of peanut allergy in the past 10 years. Jewish children in the UK, for whom peanuts were withheld during the first year of life, have a 10-fold higher prevalence of peanut allergy than similar Jewish children in Israel, for whom peanuts are consumed in high amounts during the first year of life. Current evidence suggests there is a critical "window of development" for exposure to food proteins at 4 to 6 months, coinciding with the establishment of healthy gut colonization by commensal bacteria in the developing infant.

Although it appears to be accepted among members of the relevant scientific community that regular exposure to foods on the oral cavity mucosa should begin at around 4 to 6 months, implementation remains a problem. Children's diets are very inconsistent. Thus, ensuring that children are consuming and gaining exposure to a complete spectrum of food allergens in their solid food diet is a significant challenge.

Specific embodiments of the invention provide an OMIT toothpaste formulated for FIT. A FIT-suitable OMIT toothpaste according to the invention comprises at least one food allergen, for example, an allergen sourced from one or more of the food-types that represent common food allergies that can develop in humans, including but not limited to milk, egg, soy, wheat, peanuts, tree nuts, fish and shellfish. In further specific embodiments, the OMIT toothpaste is formulated for appeal in particular to pediatric subjects. One skilled in the art would readily recognize that pediatric subjects of different ages between 4 months and 6 years of age may have varying preferences and toothpaste formulations may be designed to reflect age biases/restrictions. For example, it is recommended to avoid the use of fluoride-containing toothpaste until at least 2 years of age.

Some embodiments of the invention provides methods for diagnosing or detecting the emergence of food allergies, preferably in pediatric subjects who are not yet determined to have a food allergy or have no known clinically manifested allergy. In one embodiment, a subject who is not yet determined to have allergic food sensitivities benefits from an OMIT toothpaste containing a single food allergen which introduces the allergen to the subject's oral mucosa during regular oral care. If allergic symptoms are noted after use of the toothpaste, then the subject is suspected of having an allergic sensitivity to that allergen. The subject would stop using the toothpaste and seek additional counseling and diagnosis from a healthcare professional. The specific knowledge of the identity of the food allergen responsible for triggering the symptoms is helpful in clinical verification that an allergic sensitivity is present.

Method embodiments for diagnosing propensity to developing a food allergy in a human between the ages of 4 months and six years are also provided. The methods comprise (a) formulating a toothpaste according to claim 29 to include an allergenic protein from one food product and (b) contacting an area of the human's oral mucosa with the toothpaste formulated in step (a) in a daily regimen for a time frame; (c) monitoring for symptoms of an immune response in the oral mucosa during or after the time frame; (d) repeating steps (a), (b) and (c) until practiced with at least 1, 2, 3, up to 8 or more toothpaste formulations, one for each independent food product, and diagnosing a propensity to developing an allergy to a food product where symptoms of an immune response are observed in (c).

Other specific embodiments provide articles and kits designed to effectuate practice of methods of detecting emergence of food allergies on subjects with no current determination of clinical food allergies. According to one embodiment, a kit comprises a set of different toothpastes, each toothpaste containing a single food allergen, and each toothpaste in the series containing servings for about 1, 2, 3, or more weeks of use. In a further specific embodiment, a kit comprises a series of 8 toothpastes, each containing a single allergen from the group of 8 allergens that correspond to the 8 most common food allergies: milk, egg, soy, wheat, peanuts, tree nuts, fish and shellfish. One skilled in the art would readily recognize that pediatric subjects of different ages between 4 months and 6 years of age may have varying preferences and recommended toothpaste formulations based on age.

Subjects, as described herein, may be people who are not known to have any specific food allergy or food sensitivity. Subjects may be considered to be at risk of developing food allergies. A person who is at risk of developing food allergies may have a sibling, parent, or other family member with food allergies. A person who has exhibited other non-food allergies, for example hayfever, atopic dermatitis, or respiratory allergies may also be considered to be at risk of developing food allergies. In specific embodiments, subjects are pediatric subjects age 4 months through 6 years.

According to other specific embodiments about 0.2-1 cc of a FIT toothpaste is agitated along the teeth and gums of a pediatric patient for approximately 2 minutes, optimally with a toothbrush, bathing the vestibular mucosa with about 5, 10, 20, 30 or more mg of a single food antigen source, or alternatively as many as 8 or more food antigen sources. Smaller doses of each allergen may be appropriate for infants of 4 months to 1 year of age, for example about 1 mg, or about 5 mg, or about 10 mg, or more may be appropriate for the youngest users of FIT toothpaste. In other embodiments, amounts of each food allergen are determined as a proportion to bodyweight. For example, different formulations of FIT toothpaste may be appropriate for different age periods of subjects, with dosing of allergens corresponding to average bodyweight of subjects at those ages.

A FIT toothpaste or gel may be applied by either massaging or wiping the gums in edentulous children, or by brushing the teeth. This routine may help subjects gain tolerance to foods at a critical early stage of development, and thus help to avoid or reduce the risk of developing specific food allergies.

Food allergens comprise proteins from food sources that, in the event of contact or ingestion by an allergic individual, can trigger allergic reactions. Food allergens can also be manufactured by extraction and purification from food sources and used in various modes of AIT discussed herein and elsewhere, such as allergy shots, SLIT, and OMIT.

Methods suitable for allergen processing, e.g., production of allergen extracts, purification of allergen molecules, etc., are well known in the art. Very briefly, source allergen material (e.g., pollen, insect, dander) can be subjected initially to pulverization, drying, defatting (by extraction using organic solvent), or other steps as appropriate for the particular allergen. Centrifugation can be used, e.g., to separate solid or particulate matter. Resulting material can be incubated in an aqueous medium (e.g., water or suitable buffered solution, e.g., ammonium bicarbonate, phosphate buffered saline, etc.) for a suitable period of time to at least partly solubilize proteins. Crude extract can be processed using, e.g., dialysis, filtration, fractionation, chromatography, etc. In some embodiments, one or more steps is performed to at least partly remove low molecular weight components, concentrate the extract, etc. Extracts can be sterilized, e.g., using filtration and/or irradiation. Other processing steps can be applied as known in the art. Numerous specific protocols are available.

Extracts of allergens specifically processed for safe use in human immunotherapy are available commercially. For example, GREER Laboratories Inc. Allergy and Immunotherapy division publishes a brochure entitled "Human Allergy Products and Services" available on-line at the company website currently at http://www.greerlabs.com/files/catalogs/HumanAllergyCatalog.pdf. GREER also publishes a brochure entitled "Source Materials Products and Services" available online at the company website currently at http://www.greerlabs.com/files/catalogs/SourceMaterialsCatalog.pdf, which details available allergens that can be used as raw materials for production of allergen extracts or more highly purified allergen protein preparations. Both publications are incorporated herein by reference. Other commercial suppliers of allergens and/or allergen extracts include ALK Abello, Inc., Allermed Labs, and HollisterStier. Allergen extracts typically contain multiple proteins, e.g., multiple allergenic proteins, present in the natural form of the allergen. Extracts can be prepared from, e.g., pollens (e.g., of trees, shrubs, grasses, other plants such as those often termed "weeds"), animal epithelia, feathers, fungal mycelia or spores, smuts, mites, insects, insect venoms, foods, dusts, etc.

Allergens according to the invention are generally any allergen preparations, or combination of allergen preparations, that are suitable for AIT in allergic patients. AIT often involves the development of a specific, personalized mixture of allergens to treat an individual patient's specific allergies, according to their clinical allergy profile. This mixture is often referred to as a specific patient's "treatment set". A treatment set may comprise a single allergens or a multiplicity of different allergens, combined together.

The use of the term allergen in this disclosure can refer to a treatment set of multiple allergens or allergen extracts. In preferred embodiments, an allergen extract is provided in a liquid form, such as water, glycerin, or a combination thereof. Allergen extracts prepared for AIT are commonly provided as about 50% glycerin v/v.

There is some emerging evidence that AIT-type treatment can be used to prevent the potential development of allergies and atopic sensitivities in subjects who do not currently have allergies or allergy symptoms. Generally, the introduction of some food or other allergens, preferably at an early stage in life, has been shown to lower the risk of developing allergic sensitivities in some individuals. One of ordinary skill in the art will appreciate that methods and inventions described herein can be intended for preventative use, as well as for therapeutic use.

Subjects who benefit from the technology disclosed herein may be adult or pediatric humans who are in need AIT to treat allergic sensitivities or who may be in need of ensuring introduction of allergens to their immune systems as a way to assure development of immunotolerance and reduce the risk of developing allergies.

Importantly, the delivery of allergens via AIT modalities to treat atopic sensitivities and allergies is not limited to humans Animals, including livestock, horses, house pets, and other companion animals can also develop allergic sensitivities. AIT, both as SCIT and SLIT has been shown to be an effective tool in veterinary medicine for treating allergies in animals as well as humans. A discussion of veterinary use of AIT is available here at http://www.heska.com/Documents/Allergy/White-Paper,-Sublingual-Immunotherapy-for-Dogs.pdf and is incorporated herein by reference. Moreover, specifically formulated SCIT and SLIT products are available for AIT treatment of allergies and atopic disorders in animals, such as ALLERCEPT products (Heska, Inc., Loveland Colo.) which can be reviewed at http://www.heska.com/Products/ALLERCEPT/ALLERCEPT.aspx, incorporated herein by reference. Accordingly, subjects who may benefit from embodiments discussed herein include non-human animals.

According to one embodiment, Pro-toothpaste compositions for animal-targeted applications comprises compositions of commercially available animal toothpaste products comprising about 50% glycerin by volume. Allergens and allergen extracts may be mixed directly into the composition. Generally, animals do require the same profile of texture, rinsability, visual appearance oral sensory experience as human toothpaste consumers. Commercially available animal toothpastes contain some common elements with toothpaste compositions designed for humans, such as abrasive or polishing agents, humectants, binders, water, and flavoring. An example is the PETRODEX™ products (Sentry Pet Care Products, Inc., Omaha, Nebr.) which can be reviewed here: http://www.sentrypetcare.com/products/ProductCatalog.asp?one=1&two=171 as of Sep. 16, 2013, the disclosure of which is incorporated herein by this reference. A typical ingredient list for pet toothpaste is: sugar alcohol, purified water, dicalcium phosphate, hydrated silica, artificial beef or chicken flavor, poultry digest, dextrose, xanthan gum, and sodium benzoate.

According to some embodiments, methods for reducing allergic symptoms in an animal are provided. Methods comprise formulating an OMIT toothpaste comprising allergens or extracts of allergens suspected as the cause of the animal's symptoms, and brushing the animal's oral mucosa according to a regimen. In specific embodiments the regimen may be weekly, daily, twice daily, or more frequently depending on the allergy. In other specific embodiments allergens and/or allergen extracts may be formulated into an abrasive "tooth-brushing" toy or food-stuff as known in the art. Non-limiting examples of commercially available "chew-toys" and food-stuffs for dogs and cats may be found at http://www.petcarerx.com/search/dental%20chews%20for%20dogs.

The following examples are intended to be illustrative of specific embodiments of the invention and should not be construed as limiting the scope thereof.

EXAMPLES

Example 1

The following Example illustrates that conventional toothpaste formulations may not be mixed with allergen extract solutions without severely compromising an end-product profile, and further illustrates preliminary mixing and stability performed to provide preliminary formulation guidance. Several commercially available toothpastes with conventional active formulations, but which varied in vehicle and water percentages, were combined with white oak allergen extract (Antigen Laboratories, Inc, Liberty, Mo.), and the resulting mixtures were observed for texture and usability as toothpaste.

(1) Product 1. A well-known non-fluoridated children's toothpaste product (Product 1) was combined with white oak extract suspended in 50% glycerin v/v (Antigen Laboratories, Inc, Liberty, Mo.) at a ratio of 30 ml toothpaste and 0.6 ml of allergen extract (2% v/v). According to the label, Product 1 comprised the following listed ingredients: Purified water, sorbitol, propylene glycol, glycerin, cellulose gum, poloxamer 407, flavor, simethicone, methylparaben, potassium sorbate, sodium saccharine, propyl paraben, and citric acid. The allergens mixed into Product 1 initially, but the combination lost the texture and consistency of the original Product 1, eventually also losing its color and becoming a clear syrup over 1 week. Product 1 combined with allergens as described was unsatisfactory as toothpaste.

(2) Product 2: A commercially available fluoridated toothpaste product was combined with white oak extract in 50% glycerin v/v in the same manner and ratio (2% v/v) as previously with Product 1. According to the label, Product 2 comprised the following listed ingredients: Sodium monofluorophosphate, dicalcium phosphate dehydrate, water, glycerin, SLS, cellulose gum, flavor, tetrasodium pyrophosphate, and sodium saccharine. The allergen solution mixed with Product 2 initially, but the combination was runny and unstable, eventually separating into a solid white and a liquid phase over 48 hours. Product 2 combined with allergens was unsatisfactory as toothpaste.

(3) Product 3: A different commercially available toothpaste product was combined with white oak extract in 50% glycerin v/v in the same manner and ratio (2% v/v) as previously with Product 1 and Product 2. According to the label, Product 3 was selected as a representative silica-based composition and comprised the following listed ingredients: Sorbitol, water, hydrated silica, SLS, trisodium phosphate, flavor, sodium phosphate, cellulose gum, carbomer 956, sodium saccharine, titanium dioxide, and "Blue 1" coloring. The white oak allergen appeared to mix well with Product 3 and formulation stability was superior to other products investigated. Accordingly, the listed ingredients of Product 3 provided an initial formulation template and several specific compositions of a Pro-toothpaste formulation, each with varying percentages of ingredients and vehicle, were prepared (see Examples 2-4).

The following Examples 2-4 illustrate characteristic profiles for several preliminary Pro-toothpaste formulations.

Example 2

Formulation of PT-5
25.0% distilled water
0.33% sodium saccharine
0.58% carbomer 940
41.7% sorbitol (in 70% w/v solution)
0.83% sodium carboxymethylcellulose
1.67% sodium phosphate, tribasic
0.41% sodium fluoride
0.83% sodium phosphate, monobasic
16.7% Zeodent® 153
8.3% Zeodent® 113
0.17% titanium dioxide
1.92% sodium lauryl sulfate
Note: Percentages are based on technician's lab notes and total 98.44 total %; flavoring was not added to PT-5.
PT-5 exhibited a thick, paste-like consistency. Upon addition and thorough mixing of 1 part allergen (in 50% glycerin) to 4 parts PT-5, the consistency changed to a texture and consistency similar to that of typical toothpaste.

Example 3

Formulation of PT-7
18.2% distilled water 0.36% sodium saccharine
0.64% Carbomer™ 940
45.5% sorbitol (in 70% w/v solution)
0.91% sodium carboxymethylcellulose
1.82% sodium phosphate, tribasic
0.44% sodium fluoride
0.91% sodium phosphate, monobasic
18.2% Zeodent® 153
9.09% Zeodent® 113
0.18% titanium dioxide
2.09% sodium lauryl sulfate
0.2% peppermint oil flavor PT-7 exhibited a thick, paste-like consistency. Upon addition and thorough mixing of 1 part allergen (in 50% glycerin) to 4 parts PT-7, the consistency changed to a texture and consistency similar to that of typical toothpaste. Four volunteers were given PT-7 with allergen and asked to brush their teeth. All subjects remarked that the toothpaste was suitable as toothpaste, with consistency, texture, and flavor consistent with a typical toothpaste.

Example 4

Formulation of PT-16
22.9% distilled water
0.25% sodium saccharine
0.43% Carbomer™ 940
53.1% glycerin
0.94% sodium carboxymethylcellulose
1.23% sodium phosphate, tribasic
0.25% sodium fluoride
0.61% sodium phosphate, monobasic
12.3% Zeodent® 153
6.15% Zeodent® 113
0.12% titanium dioxide
1.41% sodium lauryl sulfate
0.25% peppermint oil flavor PT-16 exhibited a thick, paste-like consistency. Upon addition and thorough mixing of 1 part allergen (in 50% glycerin) to 4 parts PT-16, the consistency and texture sifted to that which is consistent a typical toothpaste. Four volunteers were given PT-16 with allergen and asked to brush their teeth. All subjects commented that the toothpaste was usable as toothpaste, with consistency, texture, and flavor consistent with that of typical toothpastes.

Example 5

The following Example demonstrates that a toothpaste formulated with a pro-toothpaste comprising a sugar alcohol (sorbitol, see, e.g. Example 3, PT-7) that did not correspond to the sugar alcohol aspect of the allergen extract suspension (glycerol) was unstable with respect to detectable allergen after a 1 month time frame when compared to a toothpaste formulated with a pro-toothpaste comprising a sugar alcohol corresponding to the sugar alcohol present in the allergen extract suspension (Example 4, PT-16). The exemplary allergen extracts were Der f 1, a house mite allergen extract, and Fel d 1, a cat dander extract. Each of the four aliquots of PT-7 and PT-16 was mixed with allergen extract or glycerin at a 1:4 ratio (0.5 ml allergen extract in 2 ml pre-toothpaste). Results of preliminary initial interference tests determined that the best analytical method was the Multiplex Array for Indoor Allergens (MARIA®). MARIA® is an allergen detection technology based on fluorescent microspheres coupled with monoclonal antibodies which allows the simultaneous detection of multiple allergens in a single test. Following extraction procedures described above, each sample was measured for Der f 1, Fel d 1 and Phl p 5 content using MARIA®. All 7 samples were loaded onto the plate at dilutions 1/10, 1/100 and 1/10,000. Results showing a substantial decline in concentration of allergen after one month in PT-7 versus substantial retention of allergen concentration after one month in PT-16 formulation are set forth below in Tables 1 and 2.

TABLE 1

| Pro-Toothpaste Sample | Time | Measured Der f 1 ng/ml | % Retention |
|---|---|---|---|
| PT-7 | 0 | 14.1 | |
| PT-7 | 31 days | 10.6 | 75 |
| PT-16 | 0 | 17.0 | |
| PT-16 | 31 days | 17.8 | 100 |

TABLE 2

| | | Measured Fel d 1 ng/ml | |
|---|---|---|---|
| PT-7 | 0 | 11.1 | |
| PT-7 | 31 days | 9.2 | 83 |
| PT-16 | 0 | 9.4 | |
| PT-16 | 31 days | 8.7 | 93 |

Example 6

Figure 2:
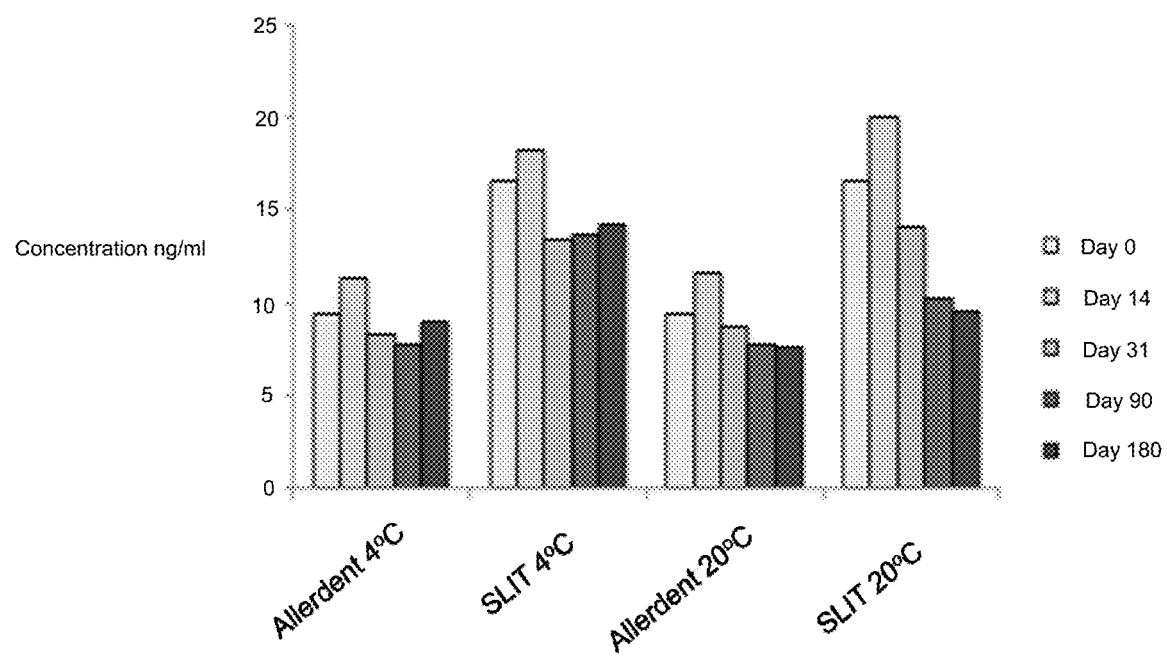
FIG. 2. A bar graph comparing stability of cat allergen extract Fel d 1 over 180 days when formulated into a toothpaste according to the invention versus Fel d 1 extract in glycerol suspension.

The following Example illustrates that toothpaste formulated with allergens according to embodiments of the invention remained stable for up to 180 days, with stability commensurate with stability of the allergen suspension solution alone, as designed for SLIT applications (an allergen extracted formulated in a 50% glycerol v/v solution). Allergen concentrations were measured and basic protocol is followed as set forth in Example 5. PT-16 formulated 4:1 with Der f 1 and PT-16 formulated 4:1 with Fel dl provided the test formulation specimens and were compared to stability of the extract alone. Results are depicted in FIG. 1 and FIG. 2. No statistical difference was observed in stability of allergens across 365 days when formulated in accordance with aspects of the invention, versus when present in allergen extract suspensions in glycerol as available for SLIT applications.

The following Examples 7-9 illustrate results of preliminary clinical investigations designed to test the efficacy of experimental OMIT toothpaste formulations in alleviating the symptoms of allergic rhinitis.

Example 7

Case Report #1 of a 42 year old female with a 25 year history of allergic rhinitis with a symptom profile of sneezing, nasal itching, and rhinorrhea in the spring, along with perennial itching in the mouth when eating apples or raw vegetables. Use of oral antihistamines only partially controlled her symptoms. She underwent skin-prick testing (SPT) for tree pollens (Grade 0 to 4 based on the diameter of the wheal at 15 minutes) with positive reactions to oak (4), elm (3), cottonwood (3), birch (4), maple (3) and ash (4). She began OMIT in February 2012, by brushing once daily for 2 minutes with 1 mL of Pro-toothpaste mixed with 0.02 mL of oak and (102 mL birch extract (Antigen Laboratories, Liberty, Mo.) delivering approximately 25 micrograms per day of each major antigen. In the first three days of treatment she experienced a tingling sensation in the mouth without swelling, but experienced no adverse reaction for the remainder of the treatment, which continued until Jun. 1, 2012. Allergy Outcome Survey was completed at baseline, mid-season (April), and in June. She did not require any medications during the treatment period for symptom control, only reporting morning congestion and skin itching intermittently in May. She reported that she was able to peel potatoes and carrots without sneezing, which she had not been able to do previously, and that her season allergies were alleviated by about "95% overall." The SPT was repeated at the end of June 2012, demonstrating a lack of skin reactivity to oak (0), while skin reactivity to birch and other tree pollens remained unchanged.

Example 8

Case Report #2 of a 39-year old female with a life-long history of perennial AR with seasonal exacerbation, resulting in sneezing, nasal congestion, rhinorrhea, and itchiness of the nose and eyes. She also reported a history of asthma and swelling of her hands when peeling carrots and potatoes. She has used oral steroids, antihistamines, and leukotriene receptor antagonists, with limited benefit and underwent a 4-year course of SCIT as a child, with limited partial control of her symptoms. She underwent SPT for tree pollen in February 2012 and tested positive for oak (4), elm (2), cottonwood (3), birch (4), maple (3) and ash (3). She was treated with an OMIT toothpaste according to the invention (Pro-toothpaste+extracts of oak and birch allergen solutions). She reported mild soreness of her gums, which resolved within 5 minutes of brushing. In March 2012 she reported that for the first time she could peel potatoes without swelling of her hands. During April and May, she reported mild itchiness, sneezing, and morning nasal congestion, which were controlled with oral anti-histamines as needed. She described her allergic symptoms as milder than what they usually are for the time of year. An SPT was repeated in June 2012 that demonstrated a decrease in skin reactivity to oak (3), while skin reactivity to the other tree pollens remained unchanged.

Example 9

Case Report #3 of a 37-year old male with a history of seasonal AR with nasal congestion, rhinorrhea and itchy eyes. Symptoms had previously been well controlled with oral antihistamines, but reports that since beginning work as a landscaper 5 years ago, he could no longer control his symptoms in the spring, despite using a nasal spray containing both a steroid and anti-histamine. SPT in 2012 was positive for oak (2) and birch (3), but negative (0) for elm, cottonwood, maple and ash. He was treated with an OMIT toothpaste according to specific embodiments of the invention, comprising oak and birch extract, from February until June 2012 and AOS were obtained at initiation, midpoint and endpoint. He reported no adverse reaction when brushing. He remained asymptomatic until May, when oral anti-histamines and topic eye drops were used successfully to control mild symptoms. SPT in June 2012 revealed a complete absence of skin reactivity to oak, but persistent reactivity to birch.

The invention claimed is:

1. A method of formulating a toothpaste suitable for oral mucosal therapy, the method comprising:
    formulating a solution comprising an allergen or allergen extract and a sugar alcohol;
    formulating a pro-toothpaste comprising:
        from about 40% to about 55% (w/w) of a sugar alcohol selected to correspond in identity to the sugar alcohol of the solution comprising the allergen or allergen extract;
        from about 10% to about 22% (w/w) of a binder;
        from about 5% to about 10% (w/w) of a silica abrasive;
        from about 0.2% to about 0.4% (w/w) of a sweetener;
        from about 1.5% to about 3% (w/w) of a preservative;
        from about 0.5% to about 1.5% (w/w) of a flavoring agent;
        from about 0.1% to about 0.2% (w/w) of an opacifier; and
        water; and
    combining the solution comprising the allergen or allergen extract and the pro-toothpaste to provide the toothpaste composition suitable for oral mucosal therapy.

2. The method according to claim 1, wherein the sugar alcohol is glycerin.

3. The method according to claim 2, wherein the toothpaste composition comprises from about 25% to about 75% (v/v) glycerin.

4. The method according to claim 1, wherein the binder comprises a carbomer, sodium carboxymethylcellulose, and a silica thickener.

5. The method according to claim 1, wherein the sweetener is sodium saccharin.

6. The method according to claim 1, wherein the preservative comprises sodium phosphate tribasic and sodium phosphate monobasic.

7. The method according to claim 1, wherein the flavoring agent is peppermint oil.

8. The method according to claim 1, wherein the opacifier is titanium dioxide.

9. The method according to claim 1, wherein the pro-toothpaste further comprises one or more of a surfactant, and anti-caries agent, and a coloring agent.

10. The method according to claim 1, wherein the allergen or allergen extract is selected from the group consisting of milk, egg, soy, wheat, peanut, tree nut, fish, shellfish, and combinations thereof.

11. The method according to claim 1, wherein the allergen or allergen extract is selected from the group consisting of animal dander, mites, white oak, maple, birch, ragweed, timothy grass, Bermuda grass, weeds, mold, fungi, and combinations thereof.

12. The method according to claim 1, further comprising pulverizing source allergen material to provide the allergen or allergen extract prior to formulating the solution comprising the allergen or allergen extract.

13. A toothpaste composition formulated by combining the solution comprising the allergen or allergen extract and the pro-toothpaste according to claim 2.

14. A toothpaste composition suitable for oral mucosal therapy, the composition comprising:
    at least one allergen or allergen extract;
    from about 40% to about 55% (w/w) of a sugar alcohol;
    from about 10% to about 22% (w/w) of a binder;
    from about 5% to about 10% (w/w) of a silica abrasive;
    from about 0.2% to about 0.4% (w/w) of a sweetener,
    from about 1.5% to about 3% (w/w) of a preservative;

from about 0.5% to about 1.5% (w/w) of a flavoring agent;

from about 0.1% to about 0.2% (w/w) of an opacifier; and water.

15. The toothpaste composition according to claim 14, wherein the allergen or allergen extract is selected from the group consisting of milk, egg, soy, wheat, peanut, tree nut, fish, shellfish, and combinations thereof.

16. The toothpaste composition according to claim 14, wherein the sugar alcohol is glycerin.

17. The toothpaste composition according to claim 14, wherein the binder comprises a carbomer, sodium carboxymethylcellulose, and a silica thickener.

18. The toothpaste composition according to claim 14, wherein the opacifier is titanium dioxide.

19. The toothpaste composition according to claim 14, wherein the pro-toothpaste further comprises one or more of a surfactant, and anti-caries agent, and a coloring agent.

20. The toothpaste composition according to claim 14, wherein the allergen or allergen extract is selected from the group consisting of animal dander, mites, white oak, maple, birch, ragweed, timothy grass, Bermuda grass, weeds, mold, fungi, and combinations thereof.

\* \* \* \* \*